(12) United States Patent
Morrison et al.

(10) Patent No.: US 6,635,439 B2
(45) Date of Patent: Oct. 21, 2003

(54) HYDROGEN PEROXIDE INDICATOR EMPLOYING ENZYME AND DYE

(75) Inventors: Todd Morrison, Newport Beach, CA (US); Veronica V. Thralls, Huntington Beach, CA (US); Franklin A. Jurik, Pleasanton, CA (US)

(73) Assignee: Ethicon, Inc., Somerville, NJ (US)

( * ) Notice: Subject to any disclaimer, the term of this patent is extended or adjusted under 35 U.S.C. 154(b) by 29 days.

(21) Appl. No.: 09/745,212

(22) Filed: Dec. 21, 2000

(65) Prior Publication Data

US 2002/0119508 A1 Aug. 29, 2002

(51) Int. Cl.[7] .............................. C12Q 1/28; C12Q 1/30; C12Q 1/26
(52) U.S. Cl. ............................. 435/28; 435/25; 435/27
(58) Field of Search ........................ 435/27, 28, 25

(56) References Cited

U.S. PATENT DOCUMENTS

| | | |
|---|---|---|
| 3,183,173 A | 5/1965 | Oakes |
| 3,298,789 A | 1/1967 | Mast |
| 3,630,957 A | 12/1971 | Rey et al. |
| RE28,575 E | 10/1975 | Bauer |
| 4,164,448 A | 8/1979 | Roeschlau et al. |
| 4,241,178 A | 12/1980 | Esders et al. |
| 4,418,037 A | 11/1983 | Katsuyama et al. |
| 4,478,942 A | 10/1984 | Katsuyama et al. |
| 4,643,876 A | 2/1987 | Jacobs et al. |
| 4,732,736 A | 3/1988 | Kobayashi et al. |
| 4,756,882 A | 7/1988 | Jacobs et al. |
| 4,786,596 A | 11/1988 | Adams |
| 4,855,228 A | 8/1989 | Charlton et al. |
| 5,059,394 A | 10/1991 | Phillips et al. |
| 5,081,044 A | 1/1992 | Buckler et al. |
| D325,442 S | 4/1992 | Lin |
| 5,139,957 A | 8/1992 | Grack |
| 5,304,468 A | 4/1994 | Phillips et al. |
| 5,409,780 A | 4/1995 | Schrier et al. |
| 5,552,320 A | 9/1996 | Smith |
| 5,563,031 A | 10/1996 | Yu |
| 5,563,042 A | 10/1996 | Phillips et al. |
| 5,710,012 A | 1/1998 | Nikolyukin et al. |
| 5,942,438 A * | 8/1999 | Antonoplos et al. .......... 422/57 |
| 6,410,338 B1 * | 6/2002 | Lippold et al. ............... 422/29 |

FOREIGN PATENT DOCUMENTS

| | | |
|---|---|---|
| DE | 19932380 A1 * | 2/2000 |
| DE | 199 25 120 A1 | 12/2000 |
| EP | 296481 A2 * | 12/1988 |
| EP | 0 769 558 A1 | 4/1997 |

OTHER PUBLICATIONS

EPO Search Report—Application No. EP 01 31 0672.9–2404—Dated May 7, 2002.

* cited by examiner

Primary Examiner—Jon P. Weber (57) ABSTRACT

A method for determining exposure of a test sample to hydrogen peroxide in an atmosphere includes placing a substrate into the atmosphere, contacting the substrate with the hydrogen peroxide, reacting the hydrogen peroxide with a dye intermediate to produce a chromophore indicative of the integrated exposure of hydrogen peroxide in the atmosphere; and correlating the chromophore to the integrated exposure of hydrogen peroxide in the atmosphere. The dye intermediate may be a dye-couple of 3-methyl-2-benzothiazolinone hydrazone hydrochloride (MBTH) and 3-dimethylaminobenzoic acid (DMAB). The intensity of the chromophore is indicative of an integrated hydrogen peroxide exposure.

16 Claims, 4 Drawing Sheets

K/S Calibration Curve @ 30 sec.

FIG. 6

Effect of H2O2 injection amount

FIG. 7

HYDROGEN PEROXIDE INDICATOR EMPLOYING ENZYME AND DYE

BACKGROUND OF THE INVENTION

The present invention relates to a method and device for detecting hydrogen peroxide.

There are many applications in which it is desirable to measure hydrogen peroxide concentration. For example in the food industry hydrogen peroxide is used to sterilize metal cans for can food preparation. Ensuring a proper application of the hydrogen peroxide to such cans is critical to maintaining proper food safety. Hydrogen peroxide is also used as a chemical disinfection agent for sterile rooms. Most importantly, hydrogen peroxide is used to sterilize industrial and medical devices. In such application, hydrogen peroxide may be applied as a liquid solution or preferably as a vapor. Hydrogen peroxide vapor may be combined with the application of a plasma field. Such systems are more fully described in U.S. Pat. Nos. 4,643,876 and 4,756,882 which are incorporated herein by reference. One such commercially available system is the STERRAD® brand sterilizer from Advanced Sterilization Products of Irvine, Calif.

In the STERRAD and similar systems, instruments to be sterilized are typically first cleaned, dried and then encased in a bacteria-proof, vapor transmisive envelope such as a TYVEK® (spun bonded olefin)/MYLAR (polyester film) pouch or central supply room wrap (CSR wrap). The instruments are placed into a sterilization chamber and gas within the chamber is evacuated to place the chamber at a vacuum pressure. Hydrogen peroxide vapor enters the chamber, and contacts the instruments to sterilize them. Power added through electromagnetic radiation or other means creates a plasma of the hydrogen peroxide, preferably at the end of the cycle. After the energy source used to create the plasma is removed, the plasma ions recombine to form oxygen and water.

The sterilization process may be checked in several ways. For instance, biological indicators may be placed in various locations through out the sterilization chamber to evaluate the sterilization process. A typical biological indicator is shown in U.S. Pat. No. 5,552,320 to Smith, incorporated herein by reference. In general, a biological indicator contains a known quantity of a living test organism. After the sterilization procedure, the organism is cultured to see whether any of the test organisms have survived the sterilization procedure. Such a culturing process necessarily entails a time delay, usually a day or more.

An alternative method of checking the operation of the sterilization cycle is to test for the presence and amount of hydrogen peroxide vapor within the sterilization chamber. If the desired amount of hydrogen peroxide is reached within the chamber, one can at least assume that the sterilization device is functioning as intended. The evaluation should preferably be instantaneous so that if a particular cycle of the sterilization process failed to achieve the necessary amount of hydrogen peroxide vapor, the cycle can be repeated immediately. Strips exist to test for the presence of hydrogen peroxide but generally are poor at evaluating the level of exposure.

SUMMARY OF THE INVENTION

The present invention provides a method and device for quickly and easily determining the presence of hydrogen peroxide and more preferably the quantity of the integrated exposure to hydrogen peroxide.

A method, according to the present invention, detects the integrated exposure of hydrogen peroxide in an atmosphere. The method comprises placing a substrate capable of absorbing hydrogen peroxide into the atmosphere, contacting the substrate with the hydrogen peroxide, reacting the hydrogen peroxide with a dye intermediate and an enzyme to produce a chromophore indicative of the integrated exposure of hydrogen peroxide in the atmosphere, and correlating the chromophore to the integrated exposure of hydrogen peroxide in the atmosphere.

Preferably, the dye intermediate comprises a dye-couple of 3-methyl-2-benzothiazolinone hydrazone hydrochloride (MBTH) and 3-dimethylaminobenzoic acid (DMAB). Also preferably, the enzyme is peroxidase.

The dye intermediate preferably comprises an oxygen acceptor, such as on of the following: O-dianisidine, O-toluidine, O-tolidine, Benzidine, 2,2'-Azinodi-(3-ethylbenzthiazoline sulphonic acid-(6)), 3-Methyl-2-benzothiazolinone hydrazone plus N,N-dimethylaniline, Phenyl plus 4-aminophenazone, Sulfonated 2,4-dichlorophenol plus 4-aminophenazone, 3-Methyl-2-benzothiazolinone hydrazone plus 3-(dimethylamino) benzoic acid, 2-Methoxy-4-allyl phenol, or 4-Aminoantipyrene-dimethylaniline.

The substrate is preferably a porous receiver. The substrate can carry the dye intermediate prior to the step of contacting the substrate with the hydrogen peroxide. Alternatively, the dye intermediate can be added onto the substrate after contacting the substrate with the hydrogen peroxide.

One method of correlating the chromophore to the integrated exposure of hydrogen peroxide in the atmosphere comprises reading the chromophore with a spectrophotometer. Alternatively, it can be compared with a color chart. Similarly, the enzyme can either be on the substrate before or after contacting the substrate with hydrogen peroxide.

The substrate can be hydrated, preferably after the step of exposing the substrate to the hydrogen peroxide. A thickening agent, such as white glue, can be added to the substrate.

The aforementioned method is particularly useful in connection with the steps of removing air from the atmosphere and generating hydrogen peroxide vapor in the atmosphere.

BRIEF DESCRIPTION OF THE DRAWINGS

The present invention can be more readily understood by reference to the following detailed description when read in conjunction with the attached drawings, wherein.

DETAILED DESCRIPTION OF THE INVENTION

Figure 1:
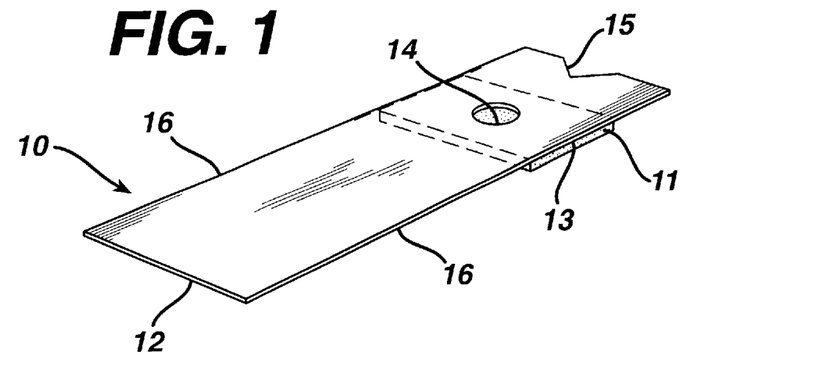
FIG. 1 is a perspective view of one embodiment of a test device according to the invention.

The subject invention provides an improved rapid and simple device and methodology for determining hydrogen peroxide exposure. As shown in FIG. 1, an indicator 10 comprises a hydrophilic matrix pad 11 to which is bound one or more reagents which change the reflectance of the matrix when hydrogen peroxide is detected. The reagents comprise an enzyme and a dye system which produces a light-absorbing product in conjunction with the enzyme. It is the light-absorbing product which changes the reflectance signal of the matrix system. Peroxidase can be used as the enzyme for this invention.

The change in reflectance over a predetermined time period as a result of formation of reaction product is then related to the amount of hydrogen peroxide on the matrix, which in turn corresponds to the integrated exposure of hydrogen peroxide, i.e. the concentration of hydrogen peroxide over the time of exposure of the matrix to the hydrogen peroxide. The integrated exposure depends on both the concentration of the hydrogen peroxide and the time length of the exposure. It is the integrated area under the concentration curve over the exposure time. Therefore, test with high peroxide concentration and short exposure time can produce the same integrated exposure with test under low concentration and long exposure time. The intensity of the light source used to analyze the sample is, of course, also carefully monitored and regulated, to insure the repeatability of the measurement.

Typically, the matrix pad 11 will be attached to a holder in order to give it physical form and rigidity, although this may not be necessary. For instance, on the indicator 10, a plastic holder or handle 12 carries the thin hydrophilic matrix pad 11 by means of an adhesive 13 which directly and firmly attaches the pad 11 to the handle 12. An aperture 14 in the plastic holder 12 adjacent the pad 11 allows liquid to be applied to one side of the pad 11 and light to be reflected from the other side.

The matrix pad 11 should be absorbent to hydrogen peroxide in a controlled manner. When exposed to a hydrogen peroxide atmosphere for a given amount of time, the amount of hydrogen peroxide absorbed into the pad 11 indicates the integrated exposure of hydrogen peroxide in the atmosphere. Several factors control how much hydrogen peroxide is absorbed by the pad, the most important being: the concentration of hydrogen peroxide in the atmosphere, the concentration of other substances such as water vapor which may be absorbed by the pad 11 and the time over which the pad 11 is exposed. The pad 11 thus exhibits an integration function relating to the hydrogen peroxide concentration over time. The total amount of peroxide absorbed into the pad 11 greatly depends on the substrate of the pad 11. Different calibration is required for different substrate. If the pad 11 is too absorbent, it may absorb too much peroxide and interfere the sterilization or disinfection process. On the other hand, if the pad 11 fails to absorb hydrogen peroxide or is easily saturated with hydrogen peroxide, it may not properly indicate the correct amount of hydrogen peroxide in the atmosphere.

A preferred material for the pad 11 comprises cellulosic material, nylon and other substrates capable of absorbing hydrogen peroxide. The use of polyamide surfaces to form the reagent element 11 provides a number of desirable characteristics in the present invention. It is hydrophilic (i.e., takes up hydrogen peroxide vapor and hydrating solutions readily), does not deform on wetting (so as to provide a flat surface for reflectance reading), is compatible with enzymes (in order to impart good shelf stability), takes up a limited sample volume per unit volume of membrane (necessary in order to demonstrate an extended dynamic range of measurements), and shows sufficient wet strength to allow for routine manufacture.

Figure 2:
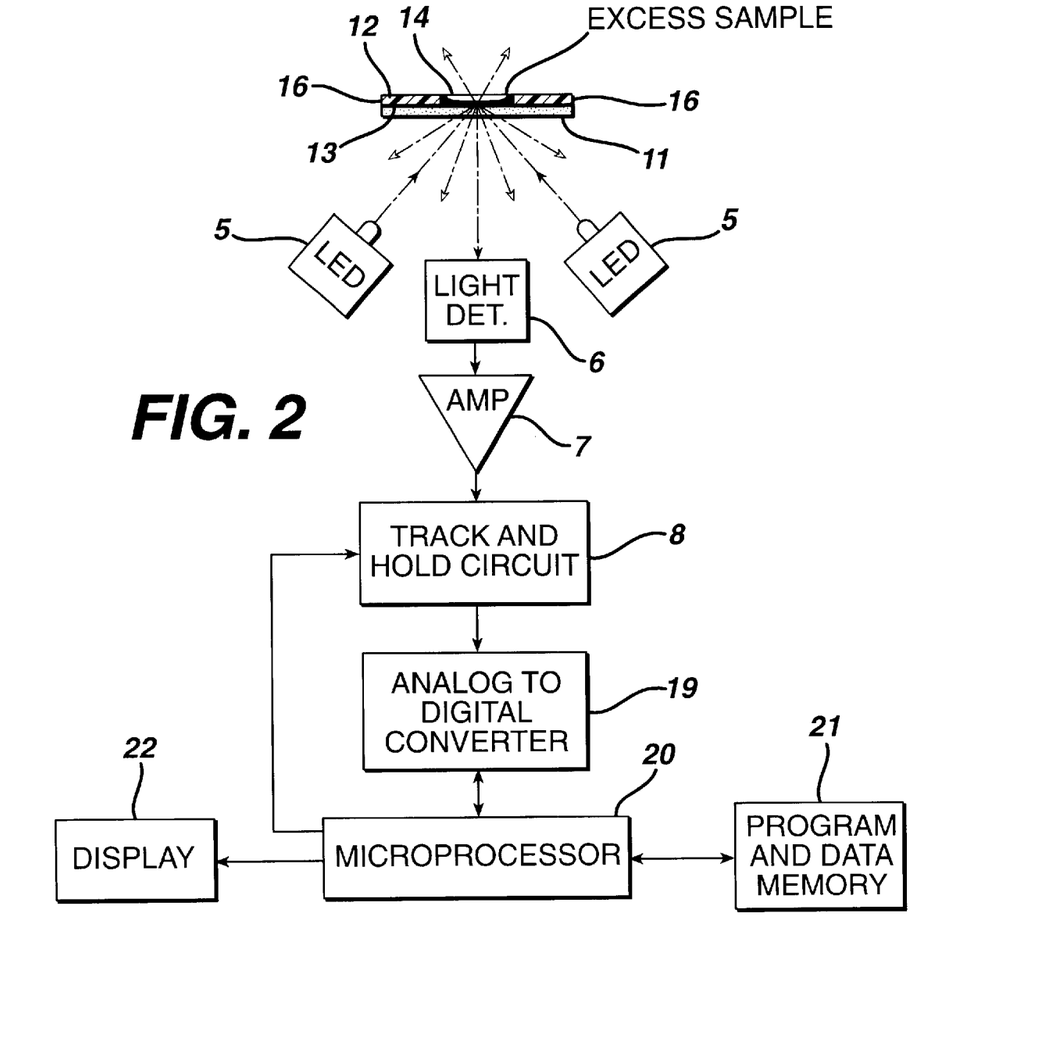
FIG. 2 is a block diagram schematic of an apparatus that can be employed in the practice of the invention.

FIG. 2 shows a system in which the reagent is applied to the side of the indicator 10 with the aperture 14 in the backing handle 12 while light is reflected and measured on the other side of the pad 11. Other structures than the one depicted may be employed. The pad 11 may take various shapes and forms, subject to the limitations provided herein. The pad 11 should be accessible on at least one surface and preferably two surfaces.

Further, the hydrophilic pad 11 can be attached to the support 12 by any convenient means, e.g., a holder, clamp or adhesives; however, in the preferred method it is bonded to the backing. The bonding can be done with any non-reactive adhesive, by a thermal method in which the backing surface is melted enough to entrap some of the material used for the hydrophilic layer, or by microwave or ultrasonic bonding methods which likewise fuse the hydrophilic sample pads to the backing.

Interaction between hydrogen peroxide and the reagents on the pad 11 produce a visual change. For instance, hydrogen peroxide can react with a dye intermediate or precursor, in a catalysed or uncatalyzed reaction, to produce an oxidized form of the intermediate or precursor. This oxidized material may produce the colored product or react with a second precursor to form the final dye. Nonlimiting examples of reagents include peroxidase and an oxygen acceptor such as: o-dianisidine; o-toluidine; o-tolidine; benzidine; 2,2'-azinodi-(3-ethylbenz-thiazoline sulphonic acid-(6)); 3-methyl-2-benzothiazoli-none hydrazone plus N,N-dimethylaniline; phenyl plus 4-aminophena-zone; sulfonated 2,4-dichloro-phenol plus 4-amino-phenazone; 3-methyl-2-benzothiazoli-none hydrazone plus 3-(dimethylamino)benzoic acid; 2-methoxy-4-allyl phenol; and 4-aminoantipyrene-dimethylaniline. Additional examples of the single indicator type include 3,3',5,5'-tetramethylbenzidine, o-toluidine and gum guaic; useful coupled indicators include 4-aminoantipyrine with 2-methyl indole, 4,5-dichloro-2-hydroxybenzenesulfonate (DCHBS) or CNSP. One common dye couple is 3-methyl-2-benzothiazolinone hydrazone hydrochloride (MBTH) and 3-dimethylaminobenzoic acid (DMAB); such dye couple and its use in a metering system for measuring blood glucose levels are described in U.S. Pat. No. 5,059,394, incorporated herein by reference. A dye couple comprising 3-methyl-2-benzothiazolinone hydrazone in free form or in acid form (MBTH) and 8-anilino-1-napthalenesulfonate, in acid or salt form (ANS) can be used in place of the common MBTH-DMAB dye couple. It is less soluble upon oxidation and, hence, provides a more stable endpoint, with minimal dye fading, as compared to the oxidized MBTH-DMAB dye couple.

U.S. Pat. No. 5,563,031, incorporated herein by reference, discloses a further reagent system comprising a dye couple capable of forming a chromophore upon being oxidized by hydrogen peroxide or another oxidizing agent; the dye couple comprising the compound:

wherein R is selected from the group consisting of alkyl, substituted alkyl, aryl, substituted aryl, heterocyclic, quaternary amine or organic acid moieties and Y is selected from the group consisting of NO2, SO3—, H, halide, alkyl or SiZ3 wherein Z is either alkyl or aryl. Preferably, Y is H. In a preferred embodiment R is:
wherein any of R1, R2 and R3 are independently selected from the group consisting of H, alkyl, aryl, silyl, halide, hydroxide, mercaptide, alkoxide, thioalkoxide, amine, sulfonate or carboxylate; and X is selected from the group consisting of amine, sulfonate or carboxylate.

The peroxidatively active substance in the test composition is preferably peroxidase obtained from natural sources such as horseradish and potato. Other substances having peroxidative activity include inorganic compounds having peroxidase activity such as mixtures of potassium iodide and sodium molybdate, as well as other iodides, such as sodium and ammonium iodides, and other molybdates, such as potassium and ammonium molybdates, can be used. In addition, urohemin and a number of other porphyrin substances having peroxidative activity can be used. Various complex-forming compounds which activate metalloporphyrins, but which are not operable per se can be used therewith, such as 2-aminobenzothiazole, pyridine, bipyridyl, bipyridylpyridine, nicotinic acid or the like. Other substances which are not enzymes but have peroxidative activity include such compounds as iron sulfocyanate, iron tannate, ferrous ferrocyanide, potassium chromic sulfate and the like.

Additional components such as buffers, surfactants and stabilizers can also be added to the composition. The pH, and therefore the addition of a buffering substance, can determine the hue of a particular form of an indicator component. For example, Acid Orange 8 is oxidized from orange to a pale straw color at pH 7.5, but is oxidized to a (pale) yellow at pH 9.5. Nitro Red is oxidized from purple to a weak brown at pH 7.5, but is oxidized to a weak blue brown at pH 9.5. One pH condition can be more desirable than another to produce the desired range of hues. Many buffering substances are known to those skilled in the art and can be used, given that they do not interfere with the action of peroxidase and hydrogen peroxide to oxidize the indicator components. Each of the above described dyes and dye couples has previously been described in the prior art with respect to analyzing serum sample analytes such as blood glucose. In such systems, a further enzyme, such as gluconase, reacts with the analyte to produce hydrogen peroxide in relation to the amount of analyte present. The above described reagents then measure the hydrogen peroxide content to determine the analyte content in the serum sample. Heretofore they were not known for measuring hydrogen peroxide exposure in an atmosphere.

The indicator 10 may be constructed and operated in several ways. For instance, it may be supplied without any reagents on the pad 11. In this embodiment, the indicator 10, without reagents, is exposed to the hydrogen peroxide atmosphere and after such exposure an aqueous solution containing the reagents, or separate solutions for each of the reagent components, are applied to the pad 11 to initiate the reaction. As will be shown below, the reaction proceeds over time and a measurement of the color change is preferably taken at a specified time after hydrating the pad 11 with the reagents. Alternatively, one or more of the reagents may be on the pad 11 while the indicator 10 is being exposed to the hydrogen peroxide atmosphere. For instance, the pad 11 may already be impregnated with the oxygen receptor prior to exposing the indicator to the hydrogen peroxide atmosphere in which case the pad need merely be hydrated with a peroxidase solution to start the reaction. The pad 11 may contain both the peroxidase and the oxygen receptor prior to exposing the indicator to the hydrogen peroxide atmosphere in which case the pad need merely be hydrated with water to start the reaction. Depending on the available amount of hydrogen peroxide and water in the atmosphere, it may be preferable to omit the peroxidase from the pad 11 until ready to start the reaction to gain better control. Too much hydrogen peroxide may inactivate or inhibit the enzyme, and too much water may initiate the reaction too early.

The analysis method of this invention preferably relies on a change in spectral absorbance, as measured by diffuse reflectance, which is dependent upon the integrated exposure of hydrogen peroxide present on the pad 11. After the indicator 10 has been exposed to a hydrogen peroxide atmosphere, the pad 11 is then hydrated in the presence of the peroxidase and oxygen acceptor thus initiating the reaction. The time to measurement may be carefully timed from the start of the hydration, or the absorbance can be measured over time to determine when the reaction has reached a predetermined point for measurement. Absorbance refers in this application not only to light within the visual wavelength range but also outside the visual wavelength range, such as infrared and ultraviolet radiation. From these measurements of absorbance a rate of color development can be calibrated in terms of hydrogen peroxide level.

A suitable instrument, such as a diffuse reflectance spectrophotometer with appropriate software, can be made to automatically read reflectance at certain points in time, calculate rate of reflectance change, and, using calibration factors, output the level of hydrogen peroxide. Such a device 60 is schematically shown in FIG. 2, with a physical embodiment shown in FIGS. 3 and 4. At least one light source 5, for example a high intensity light emitting diode (LED), projects a beam of light onto the pad 11. A substantial portion (at least 25%, preferably at least 35%, and more preferably at least 50%, in the absence of reaction product) of this light is diffusively reflected from the reagent pad and is detected by a light detector 6, for example a phototransistor that produces an output current proportional to the light it receives.

The light source 5 and/or detector 6 can be adapted to generate or respond to a particular wavelength light, if desired. The output of the detector 6 is passed to an amplifier 7, for example, a linear integrated circuit which converts the phototransistor current to a voltage. The output of the amplifier 7 can be fed to a track and hold circuit 8. This is a combination linear/digital integrated circuit which tracks or follows the analog voltage from the amplifier 7 and, upon command from a microprocessor 20, locks or holds the voltage at its level at that time.

An analog-to-digital converter 19 takes the analog voltage from the track and hold circuit 8 and converts it to, for example, a twelve-bit binary digital number upon command of the microprocessor 20. The microprocessor 20 can be a digital integrated circuit. It serves the following control functions: 1) timing for the entire system; 2) reading of the output of analog/digital converter 19; 3) together with program and data memory 21, storing data corresponding to the reflectance measured at specified time intervals; 4) calculating hydrogen peroxide levels from the stored reflectances; and 5) outputting data to a display 22. The memory 21 can be a digital integrated circuit which stores data and the microprocessor operating program. The display and reporting device 22 can take various hard copy and soft copy forms. Preferably it comprises a visual display, such as a liquid crystal (LCD) or LED display, but it can also be a tape printer, audible signal, or the like. The instrument also can include a start-stop switch and can provide an audible or visible time output to indicate times for applying samples, taking readings etc., if desired.

In the present invention, the reflectance circuit itself can be used to initiate timing by measuring a drop in reflectance that occurs when the aqueous portion of the suspension solution applied to the reagent pad 11 migrates to the surface at which reflectance is being measured. Typically, the measuring device is turned on in a "ready" mode in which reflectance readings are automatically made at closely spaced intervals (typically about 0.2 seconds) from the typically off-white, substantially dry, unreacted reagent strip. The initial measurement is typically made prior to penetration of the matrix by the hydrating fluid but can be made after the fluid has been applied to a location on the reagent element other than where reflectance is being measured. The reflectance value is evaluated by the microprocessor, typically by storing successive values in memory and then comparing each value with the initial unreacted value. When the aqueous solution penetrates the reagent matrix, the drop in reflectance signals the start of the measuring time interval. Drops in reflectance of 5–50% can be used to initiate timing, typically a drop of about 10%. In this simple way there is exact synchronization of assay medium reaching the surface from which measurements are taken and initiation of the sequence of readings, with no requirement of activity by the user.

Figures 3, 4:
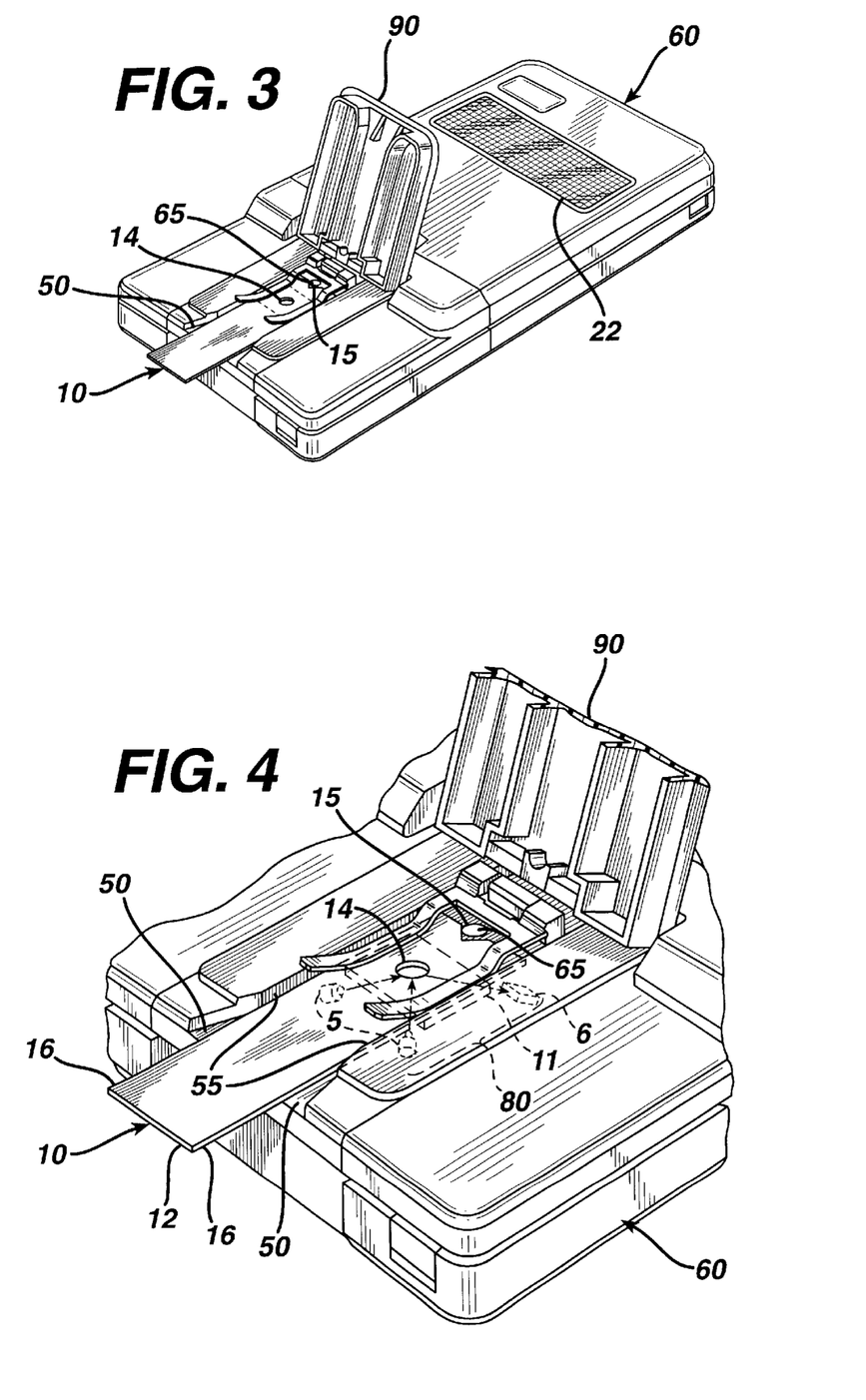
FIG. 3 is a perspective view of a preferred embodiment of the test device of the present invention placed within a measuring system.
FIG. 4 is an enlarged plan view of a preferred embodiment of the test device of the present invention placed within a measuring system.

As further seen in FIGS. 3 and 4, if desired the strip 10 can be optimally guided into a slot 50 on the scanning machine 60 by placing a notch 15 in the indicator 10 at about the midpoint of its top edge. By moving the notch 15 against a post 65, the indicator 10 will pivot around the post 65 at the notch 15, so that its edges 16 will fit within the sides 55 of the slot 50. This, of course, also repeatably aligns the hole 14 over a test center 80 comprising at least one LED 5 in the scanning machine 60. This insures that the hole 14 containing a sample will have uniform dosage of incident light for analysis.

A removable cap or other cover 90 is preferably placed over the optics to shield the assembly from ambient light. While the initialization process can begin in light, direct sunlight or high intensity room light tends to inhibit results. The cap 90, need not be light-tight, it is sufficient that it merely shield the pad 11 from direct light.

The measurement sequence is then initiated by pressing a button on the measuring apparatus that activates the microcomputer to take a measurement of reflected light from the unreacted reagent pad, called an $R_w$ reading. The cap 90 is then removed and a hydrating solution is applied to the indicator 10, typically while the reagent strip 10 is registered with the optics and the reading device. As described earlier, the hydrating solution may contain some or all of the reagents, or the reagents may be incorporated into the pad 11 allowing use of deionized water done as hydrating agent. It is preferred that the reagent strip be left in register with the optics in order to minimize handling. The cap 90 is then closed.

A particularly accurate evaluation of hydrogen peroxide level can be made using the background current, i.e., the current from the photo detector with power on but with no light reflected from the reagent pad, in order to make a background correction.

With a slight modification of the procedure, however, this value can be measured (or normalized) with each analysis for more accurate results. Each LED is turned on prior to hydration of the pad 11. A reflectance value of the indicator 10 is then measured, with the light protective cap 90 closed. If this measurement is different than the original measurement of the reflectance value, power to the LED is increased so that the reflectance will be the same. The reason for instituting this method is twofold. First, the intensity of light emitting diodes will vary greatly from LED to LED, even when the measuring LED is new. Second, the LED efficiency will vary with both temperature and the life of the LED. With this method, results are repeatable on the same scale.

The raw data necessary for calculating a result in a hydrogen peroxide assay are a background current reported as background reflectance, $R_b$, as described above; a reading of the unreacted indicator 10, $R_w$, which is about 95% opaque to light and is also described above; and an end point measurement, $R_t$. Using the preferred embodiments described herein, the end point is not particularly stable and must be precisely timed from hydration. The end point measurement, $R_t$, depends on the time from hydration. Different calibration curve is requires with different hydration time. Experimental results indicate that a 30-second reflectance reading, $R_{30}$ is adequate for determining the amount of hydrogen peroxide on the pad 11. Once the timing is determined and the calibration is established, the meter as described herein performs the measurement with the predetermined timing automatically.

The raw data are used to calculate parameters proportional to the integrated of hydrogen peroxide which can be more easily visualized than reflectance measurements. A logarithmic transformation of reflectance analogous to the relationship between absorbance and the integrated exposure of hydrogen peroxide observed in transmission spectroscopy (Beer's Law) can be used if desired. A simplification of the Kubelka-Monk equations, derived specifically for reflectance spectroscopy, has proven particularly useful. In this derivation K/S is related to the integrated exposure of hydrogen peroxide with K/S defined by Equation 1.

$$(K/S)_t = (1-R^*)^2/(2 \times R^*) \tag{1}$$

$R^*$ is the reflectivity taken at a particular end point time, t, and is the absorbed fraction of the incident light beam described by Equation 2, where $R_t$ is the end point reflectance, $R_{30}$.

$$R^* = (R_t - R_b)/(R_w - R_b) \tag{2}$$

$R^*$ varies from 0 for no reflected light ($R_b$) to 1 for total reflected light ($R_w$). The use of reflectivity in the calculations greatly simplifies meter design as a highly stable source and a detection circuit become unnecessary since these components are monitored with each $R_w$ and $R_b$ measurement.

For a single wavelength reading K/S can be calculated at 30 seconds, $(K/S)_{30}$. The calibration curves relating these parameters to Hydrogen Peroxide Integrated Exposure (HPIE) measurements can be precisely described by the third order polynomial equation outlined in Equation 3.

$$HPIE = a0 + a1(K/S) + a2(K/S)^2 + a3(K/S)^3 \quad (3)$$

Figure 5:
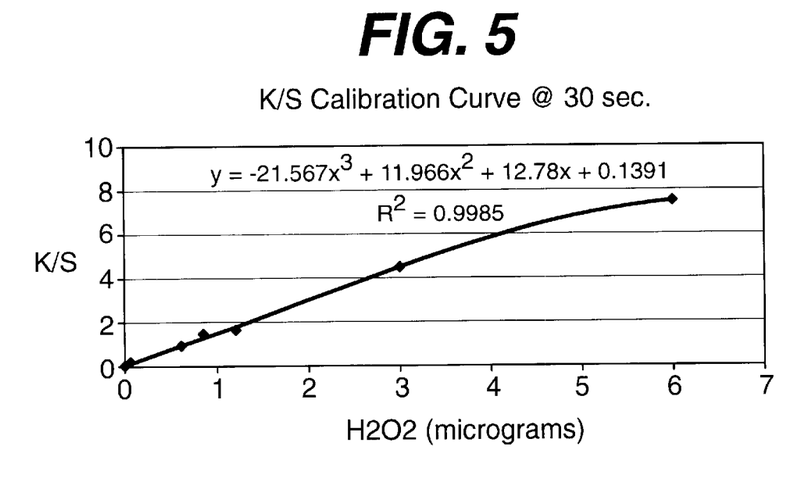
FIG. 5 is a graph plotting a calibration curve of the present invention.

Table 1 shows the background reflectance, $R_b$, the reflectance of the unreacted indicator, $R_w$, the reflectance of end point measurement after 30 seconds, $R_{30}$, the reflectivity at 30 seconds, $R^*$, and the derivation K/S at 30 seconds, $(K/S)_{30}$, with various amount of hydrogen peroxide added onto the pad 11. FIG. 5 shows the 30 seconds K/S vs. hydrogen peroxide calibration curve with the coefficients a0, a1, a2, and a3 equal to −21.567, 11.966, 12.78, and 0.1391, respectively.

TABLE 1

Coefficients for Third Order Polynomial Fit of Single Wavelength Calibration Curves

| $H_2O_2$ (microgram) | $R_{30}$ | $R_b$ | $R_w$ | $R^*$ | $(K/S)_{30}$ |
|---|---|---|---|---|---|
| 0.006 | 2598 | 40 | 4000 | 0.64596 | 0.097 |
| 0.06 | 2065 | 40 | 4000 | 0.51136 | 0.2335 |
| 0.6 | 1137 | 40 | 4000 | 0.27702 | 0.9434 |
| 0.84 | 879 | 40 | 4000 | 0.21187 | 1.4659 |
| 1.2 | 818 | 40 | 4000 | 0.19646 | 1.6432 |
| 3 | 404 | 40 | 4000 | 0.09192 | 4.4855 |
| 6 | 275 | 40 | 4000 | 0.05934 | 7.4552 |

The system 60 incorporates two diodes 5. If the diodes 5 are selected to emit light at different wavelengths, interferences in measuring the sample can be cancelled mathematically. This is more elaborately described in U.S. Pat. No. 5,304,468, incorporated herein by reference.

The invention now being generally described, the same will be better understood by reference to the following specific examples which are presented for purposes of illustration only and are not to be considered limiting of the invention unless so specified.

EXAMPLE 1

ONE TOUCH™ Strip with Hydrogen Peroxide/Gas Plasma Process

Figure 6:
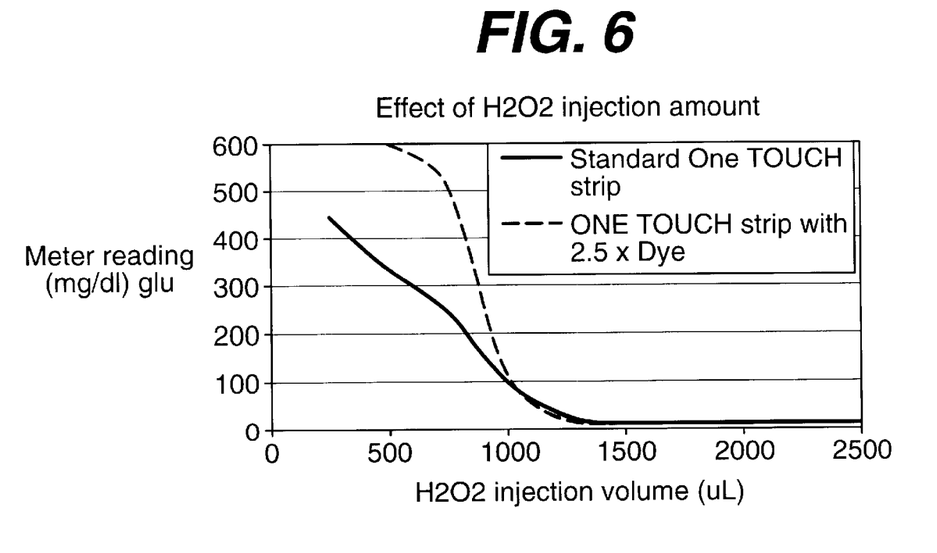
FIG. 6 is a graph plotting a measure of reflectance of a test device according to the invention versus a volume of hydrogen peroxide.

ONE TOUCH™ brand blood glucose test strips were processed in the STERRAD®100 vapor phase hydrogen peroxide/gas plasma sterilizer to try to quantify the integrated exposure of hydrogen peroxide ($H_2O_2$) diffusing into a test pack. Test packs comprise devices having an interior space which fluidly communicates to the exterior of the test pack through a diffusion restriction such as a tortuous path to simulate the difficulty in diffusing a sterilant vapor into real world devices. The test pack used for this study is similar to the U.S. Design Patent 325,442 sterilizer test pack. The TYVEK/MYLAR packaged ONE TOUCH™ strip containing dye (MBTH and DMAB) and enzyme (peroxidase) was placed at the center compartment of the test pack. Two simulated hospital loads with representative metal and plastic devices were placed in the chamber with the test pack. All strips were evaluated at 25 minutes diffusion and 15 minutes plasma cycles with different injection volumes of 59% $H_2O_2$. After each process, the strip was removed from the test pack and hydrated with water containing about 17% ELMER'S brand white glue (a polyvinyl acetate resin emulsion). The reading were taken 30 seconds after the hydrating step. The glue is used as a thickening agent such that the liquid does not spread on the strip. As shown in FIG. 6, it was observed that standard ONE TOUCH™ brand blood glucose test strips may be too sensitive for certain volumes of peroxide injected. With less than 1250 µL injection of peroxide, the indicator dye coated on the ONE TOUCH™ strips reacts with hydrogen peroxide to form a blue color with the enzymatic assistance of peroxidase after hydration. At high injection volumes of 59% H2O2 (>1250 µL), the ONE TOUCH™ brand test strips experienced a "bleaching" of the reagents coated on them. Studies were then performed to identify this "bleaching" phenomena, and to outline a more appropriate solution.

EXAMPLE 2

Increased Dye Level

To evaluate if the bleaching mechanism was a variable dependent on the amount of dye present on the strips with twice the amount of indicator dye were tested. At low injection volumes of 59% H2O2 (<1250 µL), these new strips gave about twice the color change as the regular strips (see FIG. 6). However, at higher hydrogen peroxide levels, the color formation was turned off. A definite cut off point was observed. This dye degradation may indicate another inactivation mechanism between hydrogen peroxide and the reagents. However, the inability to read processed strips was not due to insufficient indicator dye.

EXAMPLE 3

Reagent Kinetics

Figure 7:
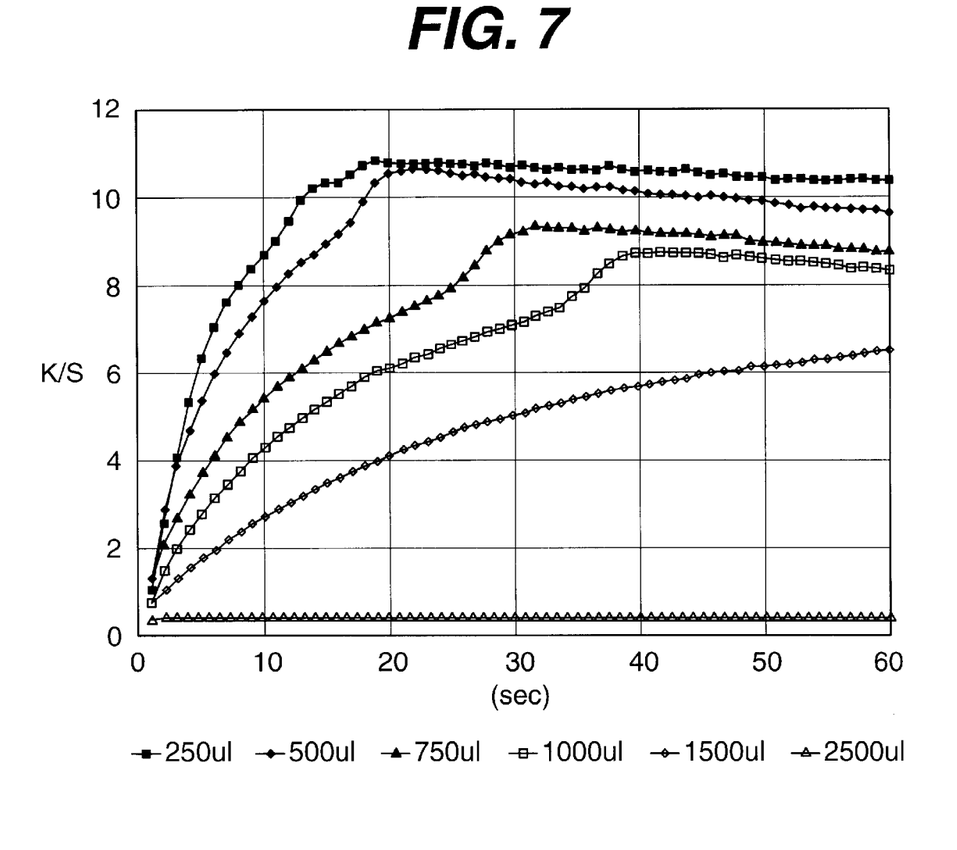
FIG. 7 is a graph showing reagent kinetics with various amount of hydrogen peroxide injected.

The rate of reaction of processed strips was also evaluated. Strips were run at half cycles (as example 1) varying the injections volumes; and then read with a meter and capture program. As shown in FIG. 7, it was clearly observed that as the integrated exposure of hydrogen peroxide increased, the rate of reaction decreased; and the mechanism was completely shut off at 2500 µL of 59% $H_2O_2$. Apparently, at high injection volume of hydrogen peroxide, one of the ingredients on the strip must be disappeared, inhibited, or inactivated during the hydrogen peroxide/gas plasma process. At low level of hydrogen peroxide injection (250 µL and 500 µL), both dye and enzyme remain on the strip still enough to produce the blue color. When more hydrogen peroxide was introduced into the chamber (750 µL, 1000 µL and 1500 µL), it took longer time to produce the blue color. This indicates that the reduction of either dye or enzyme slows down the mechanism to produce the blue color. When 2500 µL of 59% hydrogen peroxide was injected into the chamber, no blue color can be produced. Apparently, either dye or enzyme must be disappeared, inhibited or inactivated to a degree that no blue compound can be formed. As shown in the example two that increasing the dye level did not enhance the color appearance at the high volume of injection. This phenomenon points to enzyme disappearance, inactivation or inhibition by high levels of hydrogen peroxide.

EXAMPLE 4

Effect of Dye (MBTH/DMAB) and Enzyme (Peroxidase)

Ten TYVEK/MYLAR packaged ONE TOUCH™ strips were placed into ten test packs. To maximize the effect of hydrogen peroxide/gas plasma process, the cycle was conducted without the simulated load and processed at 50 minutes diffusion and 15 minutes plasma cycle through the STERRAD brand hydrogen peroxide/gas plasma sterilizer with an injection of 2500 $\mu$L of 59% $H_2O_2$, and ten unprocessed samples were subjected to a twofold analysis.

Analysis One: MBTH/DMAB Concentrations by HPLC

The amount of each of the two dye components ((MBTH and DMAB) were determined by HPLC (High Performance Liquid Chromatography) in the treated (2500 $\mu$L) and untreated ONE TOUCH™ brand test strips (Table 2). Both dye components were reduced by about 25% in the processed strips. However, based on past data this reduction should not have a significant impact on the color development of the strips. There appeared to be sufficient dye to develop treated strips at the given hydrogen peroxide levels.

TABLE 2

HPLC Analysis of Treated and Untreated Strips

|  | DMAB | MBTH |
|---|---|---|
| Untreated | 168% | 494% |
|  | 169% | 494% |
|  | 167% | 498% |
|  | Average = 168% | Average = 496% |
| Treated | 129% | 379% |
|  | 130% | 381% |
|  | 122% | 342% |
|  | Average = 127% | Average = 367% |
| % Difference | −24.4% | −25.9% |

Note that the DMAB and MBTH levels are peak areas relative to the internal standard.

Analysis Two: Peroxidase analysis by COBAS

The level of peroxidase on the strip was analyzed by the use of COBAS, an enzyme analyzer manufactured by Roche Diagnostics Corporation, Indianapolis, Ind. The peroxidase level was dramatically affected in the treated strips (Table 3). The peroxidase activity was reduced by 96.2%. This reduction in peroxidase activity would mean that high integrated exposure of hydrogen peroxide inactivate (kill) the enzyme enough to prevent the development of blue color.

TABLE 3

COBAS Analysis of Enzyme Levels

Peroxidase (units/ml)

| Untreated | Treated |
|---|---|
| 579 | 20 |
| 550 | 19 |
| 533 | 21 |
| 497 | 16 |
| 527 | 22 |
| 536 | 17 |
| 534 | 26 |
| Average of untreated = 534.3 | Average of treated = 20.1 |

% Difference between treated and untreated = −96.2%

EXAMPLE 5

Peroxidase Study and Time

Testing was conducted by processing ONE TOUCH™ brand test strips at four injection volumes (1250, 1450, 1800 and 2500 $\mu$L) in the sterilizer. Six strips were evaluated per cycle. The load and test conditions were the same as example 1. Two strips were developed immediately after cycle completion: one with DI $H_2O$ (de-ionized water) and the other with peroxidase solution (0.03% wt). At low integrated exposure of hydrogen peroxide, both diluents developed the strips (See Table 4). At higher hydrogen peroxide integrated exposure (>1500 $\mu$L), no color change was observed in the treated strips when hydrated with DI $H_2O$ (all the peroxidase was inactivated). However, a dark blue color formed instantly in the same treated strips when hydrated with peroxidase solution. This experiment confirmed that high levels of hydrogen peroxide inactivate peroxidase.

In order to understand the effect of time on the treated strips, two strips were analyzed at 24 hours and two at 48 hours. There was no color change in all the strips developed with DI $H_2O$. But, all treated strips turned dark blue in an instant when developed with peroxidase solution. This suggests that over time the hydrogen peroxide continues to kill the active peroxidase on the strips, and that hydrogen peroxide is stable on the strips at least for 48 hours after cycle completion.

TABLE 4

Qualitative Analysis of Hydrogen Peroxide Activity Over Time with Peroxidase Enzyme

| Peroxide injected | 5 min | | 24 hrs | | 48 hrs | | Comments |
|---|---|---|---|---|---|---|---|
| | DI $H_2O$ | Peroxidase | DI $H_2O$ | Peroxidase | DI $H_2O$ | Peroxidase | |
| 1250 $\mu$L | dark blue | darker blue | no change | dark blue | no change | dark blue | peroxidase - faster |
| 1440 $\mu$L | blue | darker blue | no change | dark blue | no change | dark blue | peroxidase - faster and darker color |
| 1800 $\mu$L | faint light blue | dark blue | no change | dark blue | no change | dark blue | almost no change with water |
| 2500 $\mu$L | no change | dark blue | no change | dark blue | no change | dark blue | all peroxidase is inactivated |

Comments:

The first three injection volumes at 5 min. testing changed from white to some shade of blue. However, strips developed with peroxidase changed to a much darker color blue.

Rate of reaction for strips developed with peroxidase is faster that with DI $H_2O$.

At high injection volumes (2500 $\mu$l) strips cannot be developed with DI $H_2O$. All peroxidase is inactivated.

Peroxide continues to kill peroxidase enzyme over time. Lower injections volumes (1250 µl, 1440 µl, and 1800 µl) did not developed with water (no color change) at 24 and 48 hrs. as opposed to after 5 min.

Peroxide does not leave the nylon surface of the strips over time. Strips were developed with peroxidase up to 48 hrs. after testing.

Also another test was conducted to measure the rate of reaction in the treated strips. Three injection volumes (500, 1450, and 2500 µL) were evaluated; two strips per cycle. It was observed that at lower injection volumes, strips developed with peroxidase solution were significantly faster than the strips treated with higher injection volumes. It is believe that the remaining peroxidase on the strip when treated with low level of hydrogen peroxide enhanced the development of the color. Strip treated with high integrated exposure of hydrogen peroxide can only be developed with the added peroxidase solution due to the inactivation of peroxidase on the strip during the hydrogen peroxide/gas plasma process.

It appears that peroxidase inactivation at high integrated exposure of hydrogen peroxide hinders the dye coupling reaction in the sterilization system. Understanding the actual mechanism of the reaction, modifications can be made to the strips and to the ONE TOUCH™ brand meter to obtain a quantitative reading of hydrogen peroxide present in any area of the chamber. The dye and the enzyme can be either on the strip before or added after the hydrogen peroxide or hydrogen peroxide/gas plasma process. The strip can be used to determine the amount of hydrogen peroxide either in aqueous hydrogen peroxide solution or in vapor phase hydrogen peroxide process. For vapor phase hydrogen peroxide process or hydrogen peroxide/gas plasma process, the strip needs to be hydrated after the process to initiate the color change. The hydration solution may comprise thickening agent to prevent the liquid to spread on the substrate. The thickening agent may comprise white glue or any other chemicals which increase the viscosity of the solution but does not interfere the chemical reaction or reading of the reflectance.

The invention now being fully described, it will be apparent to one of ordinary skill in the art that many modifications and changes can be made thereto without departing from the spirit or scope of the invention as defined in the following claims.

What is claimed is:

1. A method for detecting the integrated exposure of an item to hydrogen peroxide in a sterilization chamber having an atmosphere, the method comprising the steps of:

placing the item into the chamber;

placing a substrate capable of absorbing hydrogen peroxide in the chamber;

contacting the item and the substrate with the hydrogen peroxide;

hydrating the substrate in the presence of a thickening agent;

on the substrate, reacting the hydrogen peroxide with a dye intermediate and an enzyme capable of reacting with hydrogen peroxide to produce a chromophore indicative of the integrated exposure of hydrogen peroxide in the atmosphere; and correlating the chromophore to the integrated exposure of hydrogen peroxide in the atmosphere.

2. A method according to claim 1 wherein the dye intermediate comprises a dye-couple of 3-methyl-2-benzothiazolinone hydrazone hydrochloride (MBTH) and 3-dimethylaminobenzoic acid (DMAB).

3. A method according to claim 1 wherein the enzyme is peroxidase.

4. A method according to claim 1 wherein the dye intermediate comprises an oxygen acceptor.

5. A method according to claim 4 wherein the oxygen acceptor is selected from the group consisting of:

O-dianisidine;

O-toluidine;

O-tolidine;

Benzidine;

2,2'-Azinodi-(3-ethylbenzthiazoline sulphonic acid-(6));

3-Methyl-2-benzothiazolinone hydrazone plus N,N-dimethylaniline;

Phenyl plus 4-aminophenazone;

Sulfonated 2,4-dichloro-phenol plus 4-aminophenazone;

3-Methyl-2-benzothiazolinone hydrazone plus 3-(dimethylamino)benzoic acid;

2-Methoxy-4-allyl phenol; and

4-Aminoantipyrene-dimethylaniline.

6. A method according to claim 1 wherein the substrate is a porous receiver.

7. A method according to claim 1 wherein the step of correlating the chromophore to the integrated exposure of hydrogen peroxide in the atmosphere comprises reading the chromophore with a spectrophotometer.

8. A method according to claim 1 wherein the step of correlating the chromophore to the integrated exposure of hydrogen peroxide in the atmosphere comprises comparing the chromophore with a color chart.

9. A method according to claim 1 wherein the dye intermediate is on the substrate before contacting the substrate with the hydrogen peroxide.

10. A method according to claim 1 wherein the dye intermediate is added onto the substrate after contacting the substrate with the hydrogen peroxide.

11. A method according to claim 1 wherein the dye intermediate has a first color.

12. A method according to claim 1 wherein the chromophore is the appearance of a second color.

13. A method according to claim 1 wherein the chromophore is the disappearance of the first color.

14. A method according to claim 1 wherein the enzyme is on the substrate before contacting the substrate with the hydrogen peroxide.

15. A method according to claim 1 wherein the enzyme is added onto the substrate after contacting the substrate with the hydrogen peroxide.

16. A method according to claim 1 wherein the thickening agent comprises white glue.

* * * * *